United States Patent
Natura et al.

(10) Patent No.: US 7,688,444 B2
(45) Date of Patent: Mar. 30, 2010

(54) METHOD OF DETERMINING LASER STABILITIES OF OPTICAL MATERIALS, CRYSTALS SELECTED ACCORDING TO SAID METHOD, AND USES OF SAID SELECTED CRYSTALS

(75) Inventors: Ute Natura, Jena (DE); Dietmar Keutel, Mainz (DE); Lutz Parthier, Kleinmachnow (DE); Axel Engel, Ingelheim (DE)

(73) Assignee: Schott AG, Mainz (DE)

( * ) Notice: Subject to any disclaimer, the term of this patent is extended or adjusted under 35 U.S.C. 154(b) by 420 days.

(21) Appl. No.: 11/838,429

(22) Filed: Aug. 14, 2007

(65) Prior Publication Data

US 2008/0043221 A1 Feb. 21, 2008

(30) Foreign Application Priority Data

Aug. 18, 2006 (DE) .................. 10 2006 038 902

(51) Int. Cl.
*G01J 3/30* (2006.01)
(52) U.S. Cl. ........................ 356/318; 356/30
(58) Field of Classification Search .......... 356/30, 356/318
See application file for complete search history.

(56) References Cited

U.S. PATENT DOCUMENTS

| | | | | |
|---|---|---|---|---|
| 6,075,607 | A * | 6/2000 | Jinbo et al. ............... | 356/388 |
| 6,486,949 | B2 * | 11/2002 | Hachfeld et al. ........... | 356/318 |
| 6,734,970 | B2 * | 5/2004 | Wang ...................... | 356/388 |
| 7,170,069 | B2 | 1/2007 | Muehlig et al. | |
| 2001/0043331 | A1 * | 11/2001 | Rebhan ................... | 356/432 |
| 2002/0105643 | A1 * | 8/2002 | Moersen et al. ........... | 356/318 |
| 2005/0007595 | A1 * | 1/2005 | Muehlig et al. ........... | 356/432 |
| 2005/0029470 | A1 | 2/2005 | Muehlig et al. | |

(Continued)

FOREIGN PATENT DOCUMENTS

DE 103 35 457 3/2005

(Continued)

OTHER PUBLICATIONS

Kozlowski M R et al: "Luminescence Investigation of SiO2 Surface Damaged by 0.35 mm Laser Illumination" Proceedings of the SPIE—The International Society for Otpical Engineering SPIE—Int. Soc. Opt. Eng USA, BD. 3902, 2000, Seiten 138-144.. XP 002503904, ISSN: 0277-786X, 2000.

(Continued)

*Primary Examiner*—Kara E Geisel
(74) *Attorney, Agent, or Firm*—Michael J. Striker

(57) ABSTRACT

The method determines laser stability of an optical material, which is suitable for making an optical element through which high-energy light passes. The method includes pre-irradiation to produce radiation damage and measurement of the resulting induced non-intrinsic fluorescence. The method is distinguished by excitation of induced fluorescence immediately after pre-irradiation and after at least ten minutes after pre-irradiation with light of a wavelength between 350 and 810 nm, and measurement and quantitative evaluation of fluorescence intensities at wavelengths between 550 nm and 810 nm. Especially laser-stable optical materials, particularly $CaF_2$ crystals, have a normalized difference (Z) of the fluorescence intensities measured at a first time immediately after pre-irradiation and at a second time at least ten minutes after the pre-irradiation, as calculated by the following equation (1):

$$Z=(I_{2,\lambda 1,\lambda 2}-I_{1,\lambda 1,\lambda 2})/I_{2,\lambda 1,\lambda 2} \qquad (1),$$

which is less than 0.3.

8 Claims, 5 Drawing Sheets

U.S. PATENT DOCUMENTS

2005/0178316 A1 8/2005 Kandler et al.
2005/0237523 A1 10/2005 Muehlig et al.
2006/0268279 A1* 11/2006 Goenna et al. .............. 356/462

FOREIGN PATENT DOCUMENTS

DE 10 2004 003 829 8/2005
WO 2004/027395 4/2004

OTHER PUBLICATIONS

Negres R A et al: "Stoichiometric Changes 1-6 to KH2PO4 During Laser-Induced Breakdown" Proceedings of the SPIE—The International Society for Optical Engineering SPIE-—The International Society for Opticla Engineering USA, BD. 5647, NR. 1, February 21, 2005, pp. 306-312, XP002503905, ISSN: 0277-786X.

Burkert A et al: "Investigating the ARF Laser Stability of CAF2 at Elevated Fluences". Proceedings of the SPIE—The International Society for Optical Engineering, BD. 5878, NR. 1, Aug. 18, 2205. pp. 58780E-158780E-8, XP002503907.

Krajnovich D J et al: "Sudden Onset of Strong Absorption Followed by Forced Recovery in KRF Laser-Irradiated Fused Silica". Optics Letters, OSA, Optical Society of America, Washington, DC, US, BD. 18, NR. 6. Mar. 15, 1993, pp. 453-455, XP002027756, ISSN: 0146-9592.

Schermerhorn, P: "Excimer Laser Damage Testing of Optical Materials" Proceedings of the SPIE—The International Society for Optical Engineering USA, BD. 1835, 1993, pp. 70-79, XP002503906, ISSN: 0277-786X.

Negres R et al: "Evaluation of UV Absoprtion Coefficient in Laser-Modified Fudes Silica" Applied Physics Letters, AIP, American Institute of Physics, Melville, NY, BD. 90, NR. 6, Feb. 9, 2007, XP012095903, ISSN: 0003-6951.

W. Triebel, Bark-Zollmann, C. Muehlig, et al, "Evaluation of Fused Silica for DUV Laser Applications by Short Time Diagnostics", Proceedings SPIE vol. 4103, pp. 1-11, 2000.

C. Muehlig, W. Triebel, Toepfer, et al, "Calcium Fluoride for ArF Laser Lithography—Characterization by In Situ Transmission and LIF Measurements:" Proceedings SPIE vol. 4932, pp. 458-466.

M. Mizuguchi et al, "Generation of Optical Absorption Bands in CaF2 Single Crystals by ArF Excimer Laser Irradiation: Effect of Yttrium Impurity" in J. Vac. Sci. Technol. A., vol. 16, pp. 3052-3057 (1998).

M. Mizuguchi et al, I"Time-Resolved Photoluminescence for Diagnosis of Resistance to ArF Excimer Laser Damage to CaF2 Single Crystals" N J. Opt. Soc. Am. B, vol. 16, pp. 1153-1159, Jul. 1999.

* cited by examiner

METHOD OF DETERMINING LASER STABILITIES OF OPTICAL MATERIALS, CRYSTALS SELECTED ACCORDING TO SAID METHOD, AND USES OF SAID SELECTED CRYSTALS

CROSS-REFERENCE

German Patent Application DE 10 2006 038 902.6, filed Aug. 18, 2006 in Germany, describes substantially the same invention as described herein below and claimed in the claims appended herein below and provides the basis for a claim of priority for the instant invention under 35 U.S.C. 119 (a)-(d). The disclosure in the foregoing German Patent Application DE 10 2006 038 902.6 is hereby incorporated herein by explicit reference thereto.

BACKGROUND OF THE INVENTION

1. Field of the Invention

The present invention relates to a method of evaluating suitable optical material for making optical elements for high-energy radiation and to the use of the optical materials obtained by this method.

2. Description of the Related Art

It is known that materials from which optical elements are made absorb more or less of the light or radiation that passes through them, so that the intensity of the light and/or the radiation is generally less after passing through an optical element than before passing through it. It is also known that the extent of the absorption depends on the wavelength of the light. The absorption in optical systems, i.e. optically transparent systems, is kept as small as possible, because these systems should have a high light permeability or transmission, at least at their respective working wavelengths. The absorption is composed of absorption from material-specific components (intrinsic absorption) and those components, which are referred to as the so-called non-intrinsic components, such as inclusions, impurities, and/or crystal defects. While the intrinsic absorption is independent of the respective quality of the material, the additional non-intrinsic components of the absorption lead to a loss of quality of the optical material.

Energy that leads to heating is absorbed by the optical material both by intrinsic and also by non-intrinsic absorption. This sort of heating of the optical material has the disadvantage that the optical properties, such as the index of refraction, change, which leads to a change in the imaging behavior in an optical component used to beam formation, since the index of refraction not only depends on the wavelength of the light but also on the temperature of the optical material. Moreover heating of an optical component leads to a change of the lens geometry. This phenomenon produces a change of the lens focal point or to blurring of the image projected with the heated lens. This leads especially in photolithography, such as is used for making computer chips and electronic circuits, to a quality impairment or to an increase in the number of rejects. That is clearly undesirable.

Furthermore it has been shown that the absorption of the material increases with time with longer irradiation with high-energy light. This effect called radiation damage is composed of a more rapidly occurring reversible component and a slower irreversible component. In the case of the more rapid radiation damage a part of the absorbed radiation is not only converted into heat, but is output again in the form of fluorescence. The formation of fluorescence in an optical material, especially in optical crystals, is also known. For example, the production and measurement of laser-induced fluorescence (LIF) in quartz, especially in OH-rich quartz, is described in W. Triebel, Bark-Zollmann, C. Muehlig, et al, "Evaluation of Fused Silica for DUV Laser Applications by Short Time Diagnostics", Proceedings SPIE Vol. 4103, pp 1-11, 2000. Fluorescence and transmission properties of $CaF_2$ are described in C. Muehlig, W. Triebel, Toepfer, et al, Proceedings SPIE Vol. 4932, pp. 458-466. The formation of optical absorption bands in a calcium fluoride crystal is described by M. Mizuguchi, et al, in J. Vac. Sci. Technol. A., Vol. 16, pp. 2052-3057 (1998). A time-resolved photoluminescence for diagnosis of laser damage in a calcium fluoride crystal is described by M. Mizuguchi, et al, in J. Opt. Soc. Am. B, Vol. 16, pp. 1153-1159, July 1999. The formation of photoluminescence-forming color centers by excitation with an ArF excimer laser at 193 nm is described there. However so that these sorts of measurements were possible, crystals with a relatively high impurity level were used, which are insufficient for the high requirements of photolithography. Furthermore the fluorescence measurement is performed during a time interval of 50 nsec and after the laser pulse has finished passing through the sample. It has now been shown that the fluorescence values so obtained may not be used for quality control or for determination of the extent of impurity formation and thus for formation of color centers in crystals of high quality.

Since manufacture of an entire optical component from an optical blank is very expensive and labor-intensive, there is already a need to establish the extent and nature or the radiation damage that would arise in the optical component during later usage at an earlier time point, i.e. prior to working the blank. Unsuitable material must be discarded. Attempts have already been made to determine the extent and the nature of the radiation damage of this sort by means of laser-induced fluorescence. Thus, for example, WO 2004/027395 describes a process for determination of the non-intrinsic fluorescence in an optical material. In this process the fluorescence in the optical material is directly determined with the same laser, with which the pre radiation is performed, i.e. immediately after a pre-radiation with light at an excitation wavelength of 193 nm or 157 nm.

A method for quantitative determination of the suitability of optical materials is described in DE 103 35 457 A1. In this method the energy-density-dependent transmission is measured at wavelengths in the UV by determining an equilibrium value for the transmission at different fluences, measuring the slope of the curve dT/dH for this sample and comparing with the fluorescence properties.

Laser-stable material can already be evaluated at an earlier time point during production by means of the above-described method. Photolithographic illumination devices at the present stage of development require a material, which is especially laser-stable, in their illumination optics, in the laser used in them, or their laser beam guidance system. This requirement results from the productivity requirements of this sort of apparatus, which may well increase because of increases in laser power and thus inherent increases of the energy density. The sensitivity of the aforementioned short-time measuring method for pre-evaluation of suitable optical raw material is thus no longer sufficient in order to distinguish samples with especially good laser-stability from other laser-stable samples.

Material, which should have very good properties according to its later usage, must thus be constantly tested up to now in a long duration test. When this material withstood this long duration test, it could then be further processed or worked. Typical test conditions for this sort of long duration test are, for example, irradiation with a 193 nm excimer laser with a repetition rate greater than or equal to 1000 Hz at an energy density per pulse of 15 mJ/cm² and a total number of pulses of about $10^9$ pulses. That means a measurement time of about 11.5 days.

SUMMARY OF THE INVENTION

It is an object of the present invention to provide an improved evaluation method, with which laser-stable and especially laser-stabile materials can be identified or determined and especially with which samples of laser-stable and especially laser-stable material can be differentiated or distinguished from each other with regard to their laser stability.

It is another object of the present invention to provide an improved evaluation method for determining the laser stability of materials and for distinguishing laser-stable materials from each other that can be performed in a shorter time than currently available or prior art evaluation methods.

These objects, and others which will be made more apparent hereinafter, are attained in a method or determining or evaluating laser stability of optical material for making optical elements, especially for transmission of high-energy radiation, which comprises pre-irradiating the optical material to produce radiation damage and measurement of an induced non-intrinsic fluorescence.

According to the invention this method comprises the steps of:

a) pre-irradiating a sample of the material with radiation;

b) exciting induced fluorescence immediately after an end of the pre-irradiating and also at least ten minutes after the end of the pre-irradiating with light of a wavelength between 350 to 700 nm;

c) measuring intensities of the induced fluorescence at one or more wavelengths between 550 nm and 810 nm; and d) quantitatively evaluating the intensities measured in step c) at the one or more of the wavelengths between 550 nm and 810 nm.

According to the invention it has been found that the excited fluorescence in the wavelength range between 350 nm and 700 nm still changes after the end of the pre-irradiation. In the method according to the invention thus the fluorescence is not measured only immediately after the pre-irradiation as is common currently and is not excited with wavelengths used for pre-irradiation. According to the invention a first measurement is performed immediately after the pre-irradiation and a second measurement is performed after a predetermined time interval, especially after at least 5 minutes, preferably after at least 10 minutes, especially after at least 15 or 20 minutes, and especially after at least 30 minutes. Thus the increase of the fluorescence after the end of the pre-irradiation is measured. Moreover the fluorescence is not produced with the same energetic light that is used for the pre-irradiation, but with light in a wavelength range of 350 to 700 nm. Within the scope of the present invention experiments have shown that after irradiation with high-energy radiation the energy absorbed in the material leads to formation of new sodium-stabilized F-centers not presently found in crystals that have not been irradiated after a long time interval. These sodium-stabilized F-centers may be excited now by further irradiation with radiation of other wavelengths and emit fluorescence by a transition from their excited state to their ground state.

According to the invention it was found that the formation of the sodium-stabilized F-centers has an extraordinarily long formation constant (k=1/τ with τ≧10 min). This leads to an increase of the fluorescence until at least 10, especially until at least 20, preferably until at least 30 minutes after the end of the pre-irradiation.

Radiation damage (rapid damage) is usually produced by high-energy radiation. Suitable high-energy radiation sources for this purpose are, for example, X-ray sources, neutron beam sources, and high-energy lasers, e.g. an excimer laser with an energy density of ≧5 mJ/cm², e.g. 5 to >100 mJ/cm². The working wavelength range for the excimer laser is from 150 to 240 nm. A preferred laser is for example an ArF excimer laser with a wavelength of 193 nm. The irradiation is preferably performed until sufficient sodium-stabilized F-centers are formed, which is attained at the latest when equilibrium values of the transmission are reached. This equilibrium is reached usually by irradiation with about 10,000 pulses from an ArF laser (10 mJ/cm²). That equilibrium values of the transmission have been reached is established when the transmission no longer measurably changes during irradiation. The equilibrium value is reached with less than 3000 pulses, at most with 200 to 2000 pulses, at an energy density ≧or >10 mJ/cm² and with more than 200 pulses, especially more than 2000 to 3000 pulses, at an energy density <10 mJ/cm². A first measurement of the fluorescence is performed immediately after the pre-irradiation has finished. The measurement typically occurs 3 to 5 seconds after the end of the pre-irradiation and usually last for 1 second. Then the second measurement of the fluorescence, which is of the same duration as the first measurement, does not occur until at least 10 minutes, preferably at least 20 minutes, after the end of the pre-irradiation. In individual cases it has proven to be suitable to wait at least 30 minutes, as needed even at least 50 minutes. However it has been shown that the second measurement of the fluorescence should not occur later than 15 hours, especially not later than 10 hours after the end of the pre-irradiation, since relaxation processes that lead to incorrect measurement results already become noticeable. Typically the second measurement should not occur later than 8 hours after the end of the pre-irradiation.

BRIEF DESCRIPTION OF THE DRAWING

The objects, features and advantages of the invention will now be illustrated in more detail with the aid of the following description of the preferred embodiments, with reference to the accompanying figures in which.

DETAILED DESCRIPTION OF THE INVENTION

Figure 1:
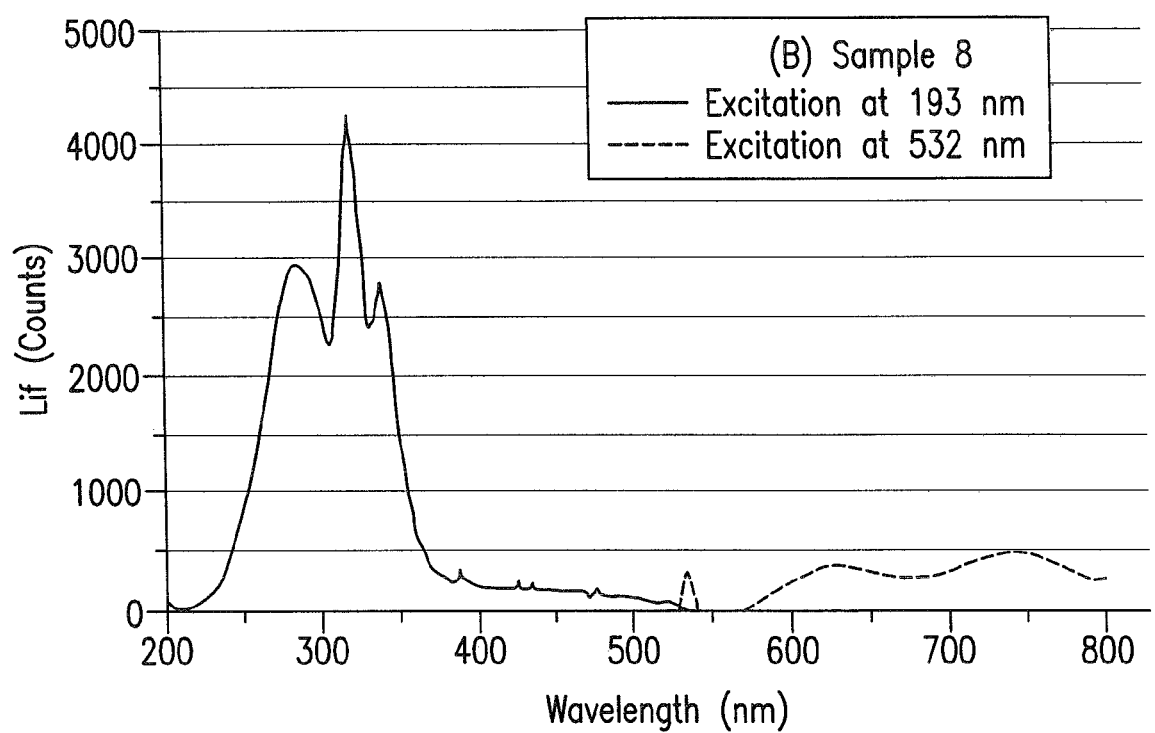
FIG. 1 shows fluorescence spectra of a laser-stable sample of a material excited with an excimer laser at a wavelength of 193 nm and excited with a DPSS laser at a wavelength of 532 nm 45 minutes after shutting off the excimer laser.

FIG. 1 shows that almost no fluorescence is measurable in the wavelength range of 550 nm to 810 nm in laser-stable samples with pre-irradiation and fluorescence measurement exclusively at 193 nm (solid curve with high peaks a to 360 nm). However according to the invention the fluorescence may still be evaluated with excitation at 532 nm (dotted curve with low peaks at 532 nm and 600 to 800 nm). Dimensionless counts are reported in FIG. 1. The qualitative behavior of these dimensionless counts remains the same although their absolute values may vary from testing set up to testing set up due to adjustment and calibration. Also the difference between prior art measurement (solid) and measurement according to the invention (dotted) remains the same from testing set up to testing set up.

It is known from the prior art that the sensitivity of the measured fluorescence in a wavelength range from 550 to 810 nm may increase still further, when the fluorescence is measured after a pre-irradiation with short-wavelength UV light. However according to the present invention the exciting wavelengths for the fluorescence measurement should not be those of the pre-irradiation, but should be in a wavelength range between 460 nm and 700 nm, especially between 500 nm and 650 nm. Measurement of the fluorescence in a wavelength range between 530 nm and 635 nm is particularly preferred. Excitation of fluorescence at wavelengths of 532 nm, 632 nm or 635 nm is particularly preferred. Furthermore a fluorescence band is satisfactorily detectable at 630 nm with excitation at wavelengths less than 600 nm. A spectrum, which was obtained with the particularly preferred excitation at 532 nm, is shown as the red curve in FIG. 1.

Excitation by means of a helium-neon laser at 633 nm or by means of a laser diode at 635 nm (besides red laser radiation, RLIF) and at 532 nm with a diode-pumped solid-state laser (DPSS laser, green laser radiation, GLIF) have proven to be especially suitable. The excitation by means of the helium-neon laser at 633 nm or by means of a laser diode at 635 nm is about a factor of 4 more sensitive than the excitation at 532 nm. In principle the fluorescence signal varies approximately linearly with the input laser power.

Figure 2A:
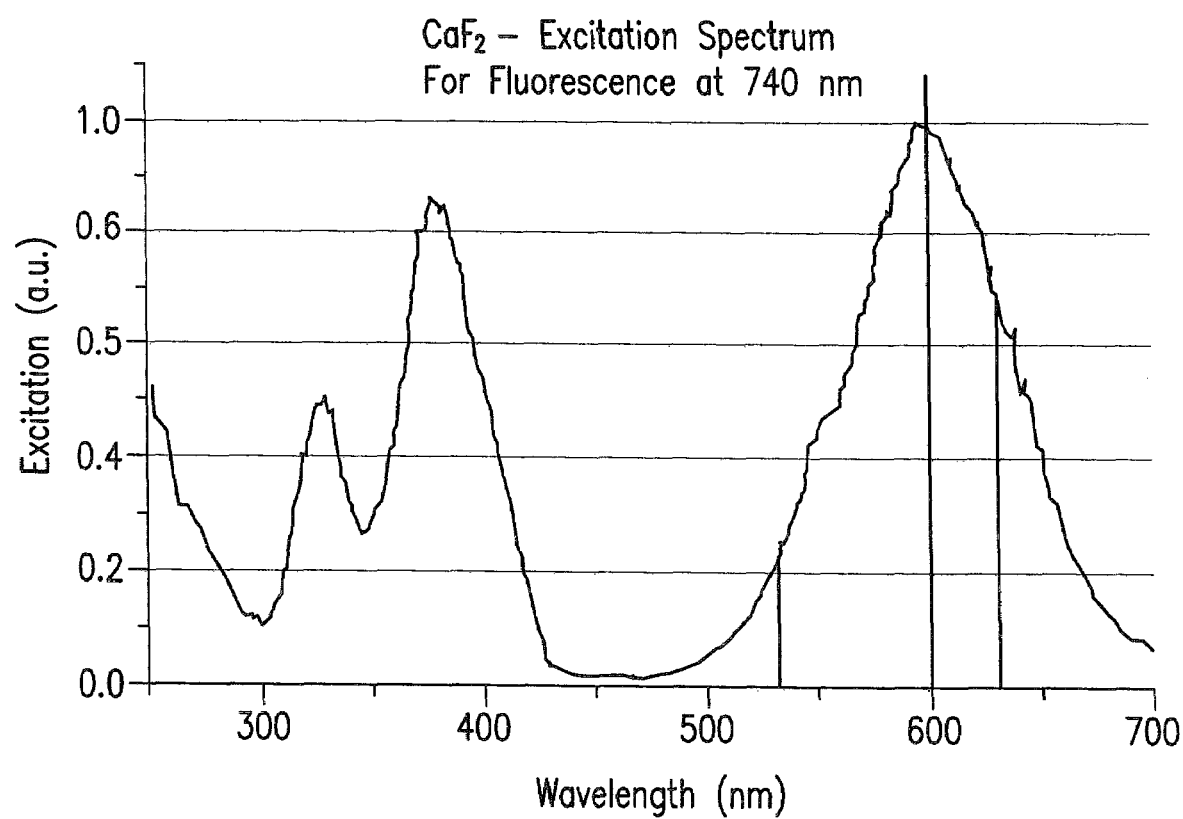
FIG. 2A shows a fluorescence excitation spectrum of $CaF_2$ for fluorescence at 740 nm measured with a fluorescence spectrometer.

FIG. 2A shows fluorescence excitation spectra for fluorescence at 740 nm with excitation with light at wavelengths of 532 nm and 633 nm respectively. At an excitation wavelength of 633 nm sensitivity improvement of about a factor of 4 is achieved in comparison to the results with excitation at a wavelength of 532 nm.

Figure 2B:
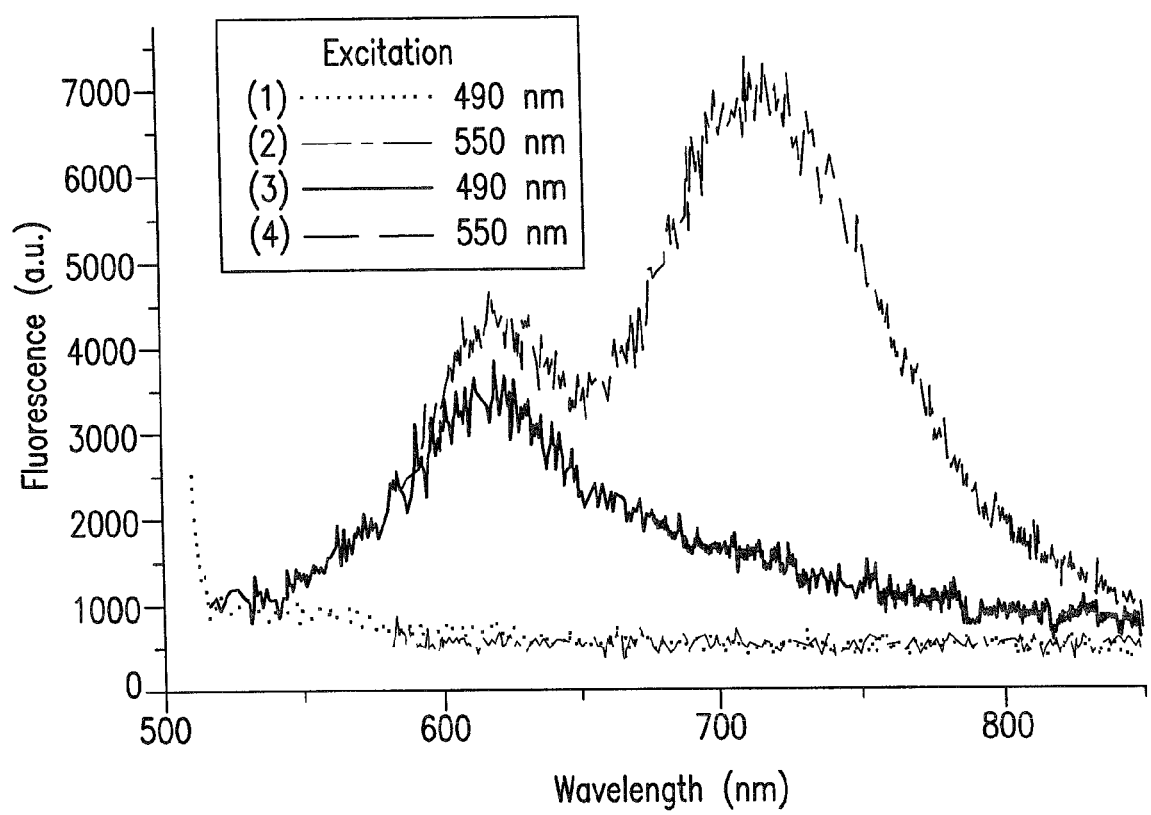
FIG. 2B shows four fluorescence spectra measured with the fluorescence spectrometer including two spectra measured with lamp excitation at 490 nm with and without pre-irradiation with a laser at 193 nm respectively and two other spectra measured with lamp excitation at 550 nm with and without pre-irradiation with a laser at 193 nm respectively.

FIG. 2B shows that both utilized preferred peaks (630 nm, 740 nm) can be controlled according to the excitation.

According to the invention especially laser-stable material is characterized in that the fluorescence does not change or only slightly changes after the end of the pre-irradiation. In contrast a less laser-stable sample already has a definite increase of the respective intensities of the fluorescence bands at 630 nm and 740 nm after a waiting time of from 10 or 20 minutes or of from 30 to 50 minutes after the end of the pre-irradiation until the second measurement. This contrasts to the first measurement, which is performed immediately after the pre-irradiation.

Both fluorescence bands are especially suitable as fluorescence measurement wavelengths within the wavelength range from 550 nm to 810 nm. In the case of fluorescence measurements of $CaF_2$ samples a wavelength of 740 nm has proven particular suitable.

In contrast to a laser-stable sample only a slight increase of the respective intensities of the fluorescence bands at 630 nm and 740 nm in comparison to the intensities measured in the first fluorescent measurement can be detected in an especially laser-stable sample by the method according to the invention under the same conditions.

Laser-stable and especially laser-stable materials may already be found in advance of working or processing by measurement of these fluorescence changes after a waiting time of at least 5 to 50 min, especially at least 10 to 30 min.

Thus the following steps occur in the method according to the invention:

1) pre-irradiation of the sample, for example with an ArF excimer laser;

2) immediately after the pre-irradiation performing a first measurement of fluorescence emission in a wavelength range λ1 of from 580 nm to 810 nm, which is excited with excitation radiation of wavelengths in a range from 460 nm to 700 nm; and 3) after a waiting time of at least 5 min, especially at least 10 min, and at most 15 hours after the end of the pre-irradiation, performing a second measurement of the fluorescence emission in a wavelength range λ1 of from 580 nm to 810 nm, which is excited with excitation radiation of wavelengths in a range from 460 nm to 700 nm.

From the measured values of fluorescence intensities the increase Z is calculated from the difference of both measured values of fluorescence intensities normalized to the intensity value measured in the second measurement ($I_{2,\lambda1,\lambda2}$) according to the following formula 1:

$$Z = (I_{2,\lambda1,\lambda2} - I_{1,\lambda1,\lambda2})/I_{2,\lambda1,\lambda2} \tag{1}$$

The value Z for especially laser-stable samples of $CaF_2$ amounts to at most 0.3 at an excitation wavelength λ1a of 532 nm or λ1b of 633 nm or 635 nm and with a measurement wavelength λ2 of 740 nm for the fluorescence.

It is even possible to already test non-crystalline pre-products, for example the calcium fluoride ingots described in DE 10 2004 003829, for their later laser resistance prior to growing finished large-volume single crystals. It is thus already possible to evaluate and identify especially suitable material prior to the expensive growth process, which lasts several months. According to the invention the three above-described method steps are employed and the same formula 1 for Z is used. In the case of $CaF_2$ the second measurement value is determined after a waiting time of at least 5 minutes, especially at least 10 minutes, preferably after at least 30 minutes, after the end of the pre-irradiation. The fluorescence excitation occurs at wavelengths λ1a of 532 nm or λ1b of 633 nm or 635 nm and with a measurement wavelength λ2 of 740 nm for the fluorescence intensities in the case of both measurements. When the Z value is less than 0.3, then the respective samples are especially laser-stable. Samples, which exhibit a signal less than 400 counts in the first and second fluorescence measurements, generally are especially laser-stable, on account of the measurement error (+150 counts, at 1500 counts −10%).

After calibration of the measurement system, comparisons of the absolute measured values of the second fluorescence measurements from sample to sample or from sample to an appropriate comparison sample are meaningful for laser resistance or laser strength classification.

The respective measured fluorescence is compared with the fluorescence of a comparison sample and with laser stability suitable for the planed application in a second embodiment of the method according to the invention. In this embodiment both samples are subjected to the same conditions, i.e. the same wavelengths and the same incident energy densities. A sample, which has fluorescence bands at 740 nm that are established as being in the signal noise of the measurement apparatus immediately after excitation at a wavelength of 193 nm according to the prior art during the fluorescence measurement, usually is used as the comparison sample for classification of the measurement probe as laser-stable. The laser resistance is measured for this comparison under conditions of usage, for example with the above-described duration of exposure to the high-energy radiation.

The method according to the invention is also used to measure the laser resistance of samples, for which a laser stability classification into laser-stable and especially laser-stable based on measured fluorescence values obtained by fluorescence measurement according to the prior art of a fluorescence band at 740 nm that is still in the signal noise of the measurement apparatus or of no band at 740 nm immediately after pre-irradiation at 193 nm is not possible. This sort of laser stability classification requires the use of the method according to the invention since a peak of $\leq 15$ counts is found using the method according to the prior art, which corresponds to the measurement error.

The optical material that has sufficient laser-stability according to the method of the present invention is especially suitable for making optical components for DUV lithography, and for making wafers coated with photo lacquer and thus for making electronic devices. The invention thus also concerns the use of materials selected or obtained by the method according to the invention and/or crystals according to the invention for making lenses, prisms, light conducting rods, optical windows and optical devices for DUV lithography, especially for making steppers and excimer lasers and thus also for making of integrated circuits, computer chips and electronic devices, such as processors and other device, which contain chip-type integrated circuits.

The inventive method is further illustrated in more detail with the following examples, whose details do not limit the appended claims.

EXAMPLES

Example 1

A 3 cm×3 cm sample was broken off of a polycrystalline ingot made from melted calcium fluoride powder. This crystal sample was irradiated in a holder with about 10,000 pulses (3 min at 60 Hz) of light with an energy density of 30 mJ/cm² from an ArF excimer laser. Subsequently immediately after pre-irradiation and after a waiting time of 20 minutes the sample was irradiated with light at 532 nm (GLIF) and the intensities of the fluorescence at a wavelength of 740 nm were measured by means of a CCD camera (Spectrometer system with CCD camera as detector). The measurement occurred by means of a CCD camera as described in the already mentioned WO 2004/027395. The normalized value of Z is calculated according to the above-described equation 1:

$$Z = (I_{2,\lambda 1,\lambda 2} - I_{1,\lambda 1,\lambda 2})/I_{2,\lambda 1,\lambda 2} \qquad (1).$$

The following measured fluorescence intensities of the fluorescence at 740 nm were obtained by excitation with wavelengths λ1a of 532 nm or λ1b of 635 nm for the different CaF₂ samples no. 1 to 5. The results are reported in Table I herein below.

TABLE 1

FLUORESCENCE INTENSITIES AT 740 nm AND CALCULATED Z VALUES FOR FLUORESCENCE OF DIFFERENT CaF₂ SAMPLES

| Sample | 1st Measurement Counts λ1a = 532 nm | 2nd Measurement Counts λ1a = 532 nm | Z | 1st Measurement Counts λ1a = 635 nm | 2nd Measurement Counts λ1a = 635 nm | Z |
|---|---|---|---|---|---|---|
| 1 | 180 | 190 | 0.05 | 380 | 410 | 0.07 |
| 2 | 500 | 3200 | 0.84 | 2000 | 14500 | 0.86 |
| 3 | 500 | 2000 | 0.75 | 1050 | 6400 | 0.85 |
| 4 | 175 | 500 | 0.65 | | | |
| 5 | 80 | 100 | 0.2 | | | |

Example 2

Figure 3A:
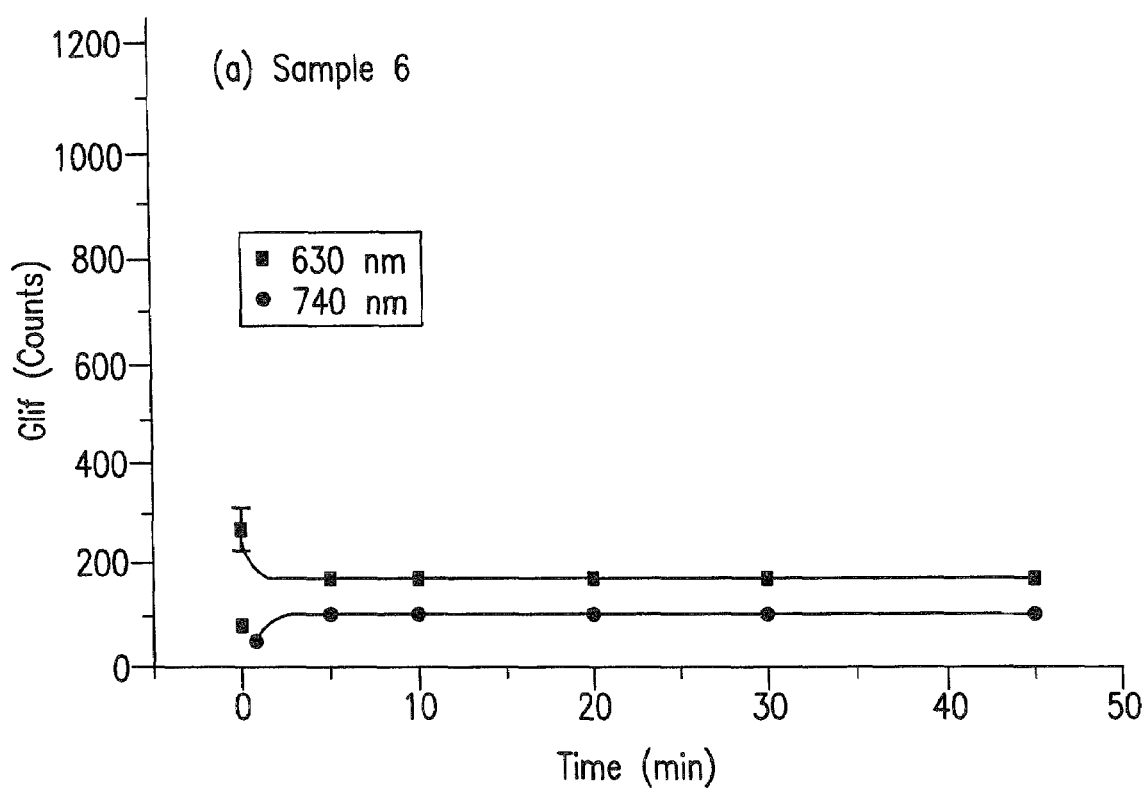
FIG. 3A is a graphical illustration of the kinetics of the GLIF at 740 nm and 630 nm respectively for a sample 6 that is very stable to high-energy laser radiation.
Figure 3B:
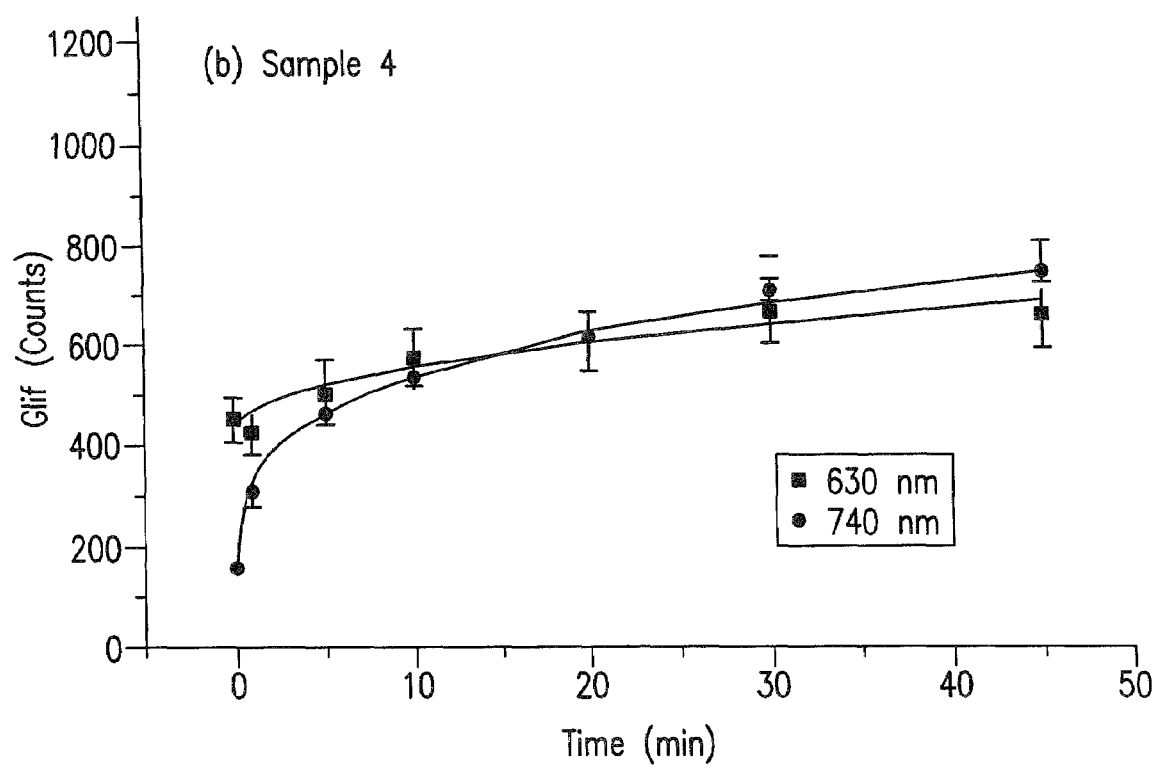
FIG. 3B is a graphical illustration of the kinetics of the GLIF at 740 nm and 630 nm respectively for a sample 4 that is stable to high-energy laser radiation, but less stable than sample 6 as shown by FIG. 3A.

A previously obtained CaF₂ crystal was pre-irradiated with 10,000 laser pulses from an ArF laser at a repetition rate of 60 Hz with an energy density of 10 mJ/cm². Subsequently this sample was irradiated with a green solid state laser with a wavelength of 532 nm and fluorescence intensities were measured immediately after pre-irradiation and also after 15, 10, 20, 30, and 45 minutes. The intensities of the fluorescence were measured at wavelengths of 630 nm and 740 nm. The results are illustrated in the appended FIGS. 3A and 3B.

While the invention has been illustrated and described as embodied in a method of determining the laser stability of optical materials, crystals selected according to the method, and uses of the selected crystals, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

We claim:

1. A method of determining or evaluating laser stability of optical materials for making optical elements, in which the optical materials are pre-irradiated and induced non-intrinsic fluorescence of the optical materials is measured, said method comprising the steps of:
   a) pre-irradiating an optical material;
   b) exciting induced fluorescence in the optical material immediately after an end of said pre-irradiating and also at least ten minutes after said end of said pre-irradiating with light of a wavelength between 350 to 700 nm;
   c) measuring intensities of said induced fluorescence at one or more wavelengths between 550 nm and 810 nm; and d) quantitatively evaluating said intensities of said induced fluorescence at said one or more of said wavelengths between 550 nm and 810 nm.

2. The method as defined in claim 1, in which said wavelength that excites said induced fluorescence in said optical material is between 350 nm and 430 nm or between 500 nm and 700 nm.

3. The method as defined in claim 1, in which said pre-irradiating of said optical material takes place with radiation from a laser and said radiation from said laser is in a wavelength range from 150 nm to 240 nm.

4. The method as defined in claim 3, in which said radiation from said laser is at 193 nm and said laser is an ArF excimer laser.

5. The method as defined in claim 1, in which said wavelengths at which said intensities of said induced fluorescence are measured are between 580 nm and 810 nm and/or between 680 nm and 810 nm.

6. The method as defined in claim 1, in which said fluorescence intensities are measured at a first time immediately after said end of said pre-irradiating and at a second time after waiting for at least 5 minutes and at most 15 hours after said end of said pre-irradiating.

7. The method as defined in claim 1, wherein said optical material is a $CaF_2$ crystal.

8. A method of finding at least one especially laser-stable $CaF_2$ crystal in a group of calcium fluoride crystals, said method comprising the steps of:

a) pre-irradiating each of a plurality of different $CaF_2$ crystals;

b) exciting induced fluorescence in each of the different $CaF_2$ crystals immediately after an end of said pre-irradiating and also exciting the induced fluorescence at least ten minutes after said end of said pre-irradiating with light of a wavelength between 350 to 700 nm;

c) measuring intensities of said induced fluorescence in each of the different samples at a wavelength of 740 nm in a first measurement at a first time immediately after said end of said pre-irradiating and in a second measurement at a second time after waiting for at least 10 minutes and at most 15 hours after said end of said pre-irradiating; and d) identifying the at least one $CaF_2$ crystal that is especially laser-stable as having a normalized difference (Z) of said intensities ($I_{1,\lambda1,\lambda2}, I_{2,\lambda1,\lambda2}$) of said induced fluorescence measured in said first measurement and in said second measurement, as calculated by the following equation (1):

$$Z = (I_{2,\lambda1,\lambda2} - I_{1,\lambda1,\lambda2})/I_{2,\lambda1,\lambda2} \qquad (1),$$

that is less than 0.3.

* * * * *